United States Patent [19]
Aoki et al.

[11] Patent Number: 6,034,236
[45] Date of Patent: Mar. 7, 2000

[54] METHOD FOR PRODUCING OF PHTHALOCYANINE COMPOUND

[75] Inventors: Minoru Aoki; Osamu Kaieda, both of Ibaraki, Japan

[73] Assignee: Nippon Shokubai Co., Ltd., Osaka-fu, Japan

[21] Appl. No.: 09/092,719

[22] Filed: Jun. 5, 1998

[30] Foreign Application Priority Data

Jun. 5, 1997 [JP] Japan ................................. 9-148101
Jan. 16, 1998 [JP] Japan ................................. 10-007020

[51] Int. Cl.$^7$ .......................... C09B 47/10; C09B 47/067
[52] U.S. Cl. .......................... 540/143; 540/122; 540/136; 540/137; 540/139
[58] Field of Search .................... 540/143, 137, 540/139, 122, 136

[56] References Cited

U.S. PATENT DOCUMENTS

| | | | |
|---|---|---|---|
| 4,557,868 | 12/1985 | Page et al. | 260/249.89 |
| 4,771,133 | 9/1988 | Liebermann et al. | 540/143 |
| 5,270,463 | 12/1993 | Itoh et al. | 540/136 |
| 5,663,326 | 9/1997 | Wolleb | 540/139 |

FOREIGN PATENT DOCUMENTS

| | | | |
|---|---|---|---|
| 0602076 | 7/1960 | Canada . | |
| 0 166 569 | 1/1986 | European Pat. Off. | C09B 47/067 |
| 0 464 959 A2 | 1/1992 | European Pat. Off. | C07D 487/22 |
| 0 523 959 A2 | 1/1993 | European Pat. Off. | C09B 47/08 |
| 0017430 | 6/1973 | Japan . | |
| 3-269063 | 11/1991 | Japan . | |
| 06041137 | 2/1994 | Japan . | |
| 06256680 | 9/1994 | Japan . | |
| 07036205 | 2/1995 | Japan . | |
| 783157 | 9/1957 | United Kingdom . | |
| 1037657 | 8/1966 | United Kingdom | C09B 47/04 |
| WO 97/28969 | 8/1997 | WIPO | B41M 5/40 |

*Primary Examiner*—Mukund J. Shah
*Assistant Examiner*—Pavanaram K Sripada
*Attorney, Agent, or Firm*—Fish & Richardson P.C.

[57] ABSTRACT

A method for producing a novel phthalocyanine compound which excels in yield and purity, allows no introduction of a chlorine atom into the phthalocyanine skeleton, and possesses relatively bulky substituents is provided. This method is characterized by causing an orthophthalonitrile compound having a substituent exhibiting smaller $\sigma_p$ values than $\sigma_m$ values in the Hammett's rule to react with a metal oxide in the presence of a compound forming in the aqueous solution thereof at 25° C. an acid or conjugate acid having a dissociation index pKa (the logarithmic value of the reciprocal of the dissociation constant of the acid or conjugate acid) of not more than 7.0.

10 Claims, No Drawings

METHOD FOR PRODUCING OF PHTHALOCYANINE COMPOUND

BACKGROUND OF THE INVENTION

1. Field of the Invention

This invention relates to a method for producing of a novel phthalocyanine compound. More particularly, it relates to a method for producing of a phthalocyanine compound which has an absorption in a near infrared zone and exhibits high solubility to solvents. Since the phthalocyanine compounds to be obtained by the method of the production according to the present invention have absorption in the near infrared zone of 600–1000 nm, they manifest excellent effects when they are used as near infrared absorption materials e.g. near infrared absorption dyes, near infrared sensitizers, thermal transfer inks, photothermal conversion agents for thermosensible papers and screen printing papers, PDP grade near infrared absorption filters, asthenopic preventives, and photoconductive materials intended for the operation of writing or reading in optical recording devices, liquid crystal display devices, and optical character reading device which utilize a semiconductor laser or as color separation filters for image pickup tubes, color filters for liquid crystal display, selective absorption filters for color braun tubes, color toners, flush fixing grade toners, thermal jet grade inks, indelible bar code inks, microbe-inactivating agents, photosensitive dyes for the therapy of ulcers, and heat ray insulators or heat retaining agents for automobiles or building materials. The phthalocyanine compounds which are obtained by the method of the production according to this invention manifest outstanding effects particularly when they are used as optical recording media e.g. compact discs, laser discs, optical memory discs, and optical cards, liquid crystal display grade color filters, PDP grade near infrared absorption filters, or heat ray insulators.

2. Description of Related Art

The recent years have been witnessing active development of such optical recording media as compact discs, laser discs, optical memory discs, and optical cards which utilize the semiconductor laser as their light sources. Particularly, CD, PHOTO-CD, and CD-ROM have been being used in large quantities as digital recording media of high capacity and rapid access for the storage and regeneration of voices, images, and coded data. These systems invariably necessitate so-called near infrared absorption dyes which are sensitive to the semiconductor laser. As regards these dyes, the desirability of their having excellent characteristics has been finding widespread recognition. Such phthalocyanine compounds as are stable enough to resist light, heat, and excellent in strength, among other species of phthalocyanine compound, are now undergoing numerous studies which are devoted to imparting thereto the solubility in solvents which is needed to suit the purpose for which the compounds are used. Specifically, methods for forming thin films of dyes without requiring such complicated steps as vacuum deposition or dispersion in resin, methods for selectively using such solvents as are incapable of corroding substrates used in the relevant devices being manufactured, and methods for enabling dyes to be solved in high concentrations in various species of solvents fit for various applications in the light of the fact that they also dissolve in the resins being used have been the subjects for such studies.

The so-called grazing materials for use in buildings or vehicles are in need of a light-shielding agent which is capable of intercepting heat rays. Since phthalocyanine compounds are rich in resistance to heat and lightfastness, they have been proposed in numerous types. Further, phthalocyanine compounds of varying types have been proposed for use as dyes in liquid crystal display grade color filters and in PDP grade near infrared cut filters.

Orthophthalonitrile is reacted with a metal source in a synthesis of a method for phthalocyanine compounds by using orthophthalonitrile. As the metal source, generally, halogenide, oxide, salt of organic acid, metal powder are cited. Among them, halogenide is used to the reaction because of having high reactivity generally. There were, however, some problems that halogen atoms were mixed to a skeleton of phthalocyanine, or an equipment made of special material was needed because of generation of halogen gas by using halogenide of the reaction for synthesis of phthalocyanine. Instead of it, a means for synthesizing the phthalocyanine compound, the method which use an oxide as a metal source is also proposed. There are examples of producing a vanadyl phthalocyanine by using vanadium pentaoxide(JP-A-06-256680, JP-A-07-36205, U.S. Pat. No. 4,771,133, Jp-A-03-269063, U.S. Pat. No. 4,557,868 and JP-A-06-41137). Among them, although JP-A-06-256680 and JP-A-07-36205 were disclosed a method which used α-chloronaphthalene as solvent, it had a problem that yield of vanadyl phthalocyanine didn't raise because of lower solubility based on little solubility to α-chloronaphthalene. On the one hand, U.S. Pat. No. 4,771,133, JP-A-03-269063, U.S. Pat. No. 4,557,868 and JP-A-06-41137 were disclosed a method which used ethylene glycol as solvent, the method was reacted with an intermediate of causing the reaction with phthalonitrile and ethylene glycol. Certainly this method raised a reactivity for using an intermediate, it had a problem that a purification process was complicated because of an inferior selectivity to produced phthalocyanine compound.

In recent years, a phthalocyanine compound having high solubility in solvents was desired, a general method to solve the problem to displace the extent of a bulky substituent onto benzene ring of a skeleton of phthalocyanine. There was no example using a metal oxide as a source metal for synthesis of phthalocyanine compound having the extent of a bulky substituent. It is because that the orthophthalonitrile compound having a little bulky substituent has an inferior reactivity comparing to orthophthalonitrile compound having no or smaller substituent because of a stereo impediment. For overcoming the issue, a high reactivity of halogenide would be used for synthesis of the phthalocyanine compound having the extent of a bulky substituent. Using a halogenide, there were problems that a substituent was reacted with halogen atoms, and the natural property of phthalocyanine compound was damaged because of bonding a halogen atom to skeleton of phthalocyanine compound. Accordingly, a development for synthesis of phthalocyanine compound using a metal oxide compound as a metal source was desired.

It is, therefore, an object of this invention to provide a method for producing a phthalocyanine compound, which is characterized by causing an orthophthalonitrile compound possessable of a substituent to react with a metal oxide in the presence of a compound forming in the aqueous solution thereof at 25° C. an acid or conjugate acid having a dissociation index pKa (the logarithmic value of the reciprocal of the dissociation constant of the acid or conjugate acid) of not more than 7.0. Specially to provide a useful method for producing a phthalocyanine compound having substituent capable of increasing a solubility.

Another object of this invention is to provide a method for the production of a phthalocyanine compound possessable of a substituent, which compound excels in yield and purity.

SUMMARY OF THE INVENTION

The present inventors, on realizing that the conventional methods which simply use a metal oxide or metal chloride as a metal source are unfit for the production of a phthalocyanine compound excelling in purity and quality and possessing practically significant solubility in solvents, have continued a diligent study with a view to accomplishing the objects mentioned above. The present invention has been perfected as a result.

Specifically, the objects of this invention are fulfilled by (1) a method for producing a phthalocyanine compound, which is characterized by causing an orthophthalonitrile compound possessable of a substituent to react with a metal oxide in the presence of a compound forming in the aqueous solution thereof at 25° C. an acid or conjugate acid having a dissociation index pKa (the logarithmic value of the reciprocal of the dissociation constant of the acid or conjugate acid) of not more than 7.0.

The objects of this invention are fulfilled by (2) the method mentioned (1), wherein said orthophthalonitrile compound possessable of a substituent is the orthophthalonitrile compound having a substituent exhibiting smaller $\sigma_p$ values than $\sigma_m$ values in the Hammett's rule.

The other objects of this invention are fulfilled by (3) the method mentioned (2), wherein said substituent exhibiting smaller $\sigma_p$ values than $\sigma_m$ values in the Hammett's rule is at least one member selected from the class consisting of halogen atoms, $-R^1$, $-NHR^2$, $-NR^3R^4$, $-OR^5$, and $-SR^6$, and said each $R^1-R^5$ is an alkyl group or aryl group possessable of a substituent.

The other objects of this invention are fulfilled by (4) the method mentioned any of (1)–(3), wherein said metal oxide is the oxide of a metal having valence of not less than 2.

The other objects of this invention are fulfilled by (5) the method mentioned any of (1)–(4), wherein said compound forming in the aqueous solution thereof at 25° C. an acid or conjugate acid having a dissociation index pKa of not more than 7.0 is an organic acid compound.

The other objects of this invention are fulfilled by (6) the method mentioned any of (1)–(5), wherein said reaction is carried out in an organic solvent.

The method of production according to this invention, owing to the use of a metal oxide [vanadium trioxide ($V_2O_3$) in particular] as the raw material for a metal salt and the novel use of a compound (preferably an organic acid, particularly an organic sulfonic acid compound, and specifically p-toluene-sulfonic acid) exhibiting in the aqueous solution thereof at 25° C. a pKa value (the logarithmic value of the reciprocal of the dissociation constant of an acid or conjugate acid) of not more than 7.0, manifests the peculiar effect of enabling a phthalocyanine compound which possesses a catalytic function and precludes inclusion in the phthalocyanine compound of such extraneous substances as halogen atoms besides the designed substituents and consequently succumbs to purification without any complication to be produced in a high yield with high purity in spite of the incorporation therein of a relatively bulky substituent rather inexpensively as compared with the conventional phthalonitrile method of synthesis.

DESCRIPTION OF THE PREFERRED EMBODIMENT

The method for the production of a phthalocyanine compound according to this invention uses a metal oxide as a metal source. This novel method of production has originated in the discovery that the conventional methods of production using a metal oxide (JP-A-06-256680, JP-A-07-36205, U.S. Pat. No. 4,771,133, JP-A-03-269063, and U.S. Pat. No. 4557868) is not an example of displacing a bulky substituent to a skeleton of phthalocyanine, as well as not sufficient for practical use thereof.

Specifically, the method of the present invention for producing a phthalocyanine compound, which is characterized by causing an orthophthalonitrile compound possessable of a substituent to react with a metal oxide in the presence of a compound forming in the aqueous solution thereof at 25° C. an acid or conjugate acid having a dissociation index pKa (the logarithmic value of the reciprocal of the dissociation constant of the acid or conjugate acid) of not more than 7.0. Preferably, said orthophthalonitrile compound is the compound having a substituent exhibiting smaller $\sigma_p$ values than $\sigma_m$ values in the Hammett's rule.

The present invention was established by finding that a compound forming in the aqueous solution thereof at 25° C. an acid or conjugate acid having a dissociation index pKa (the logarithmic value of the reciprocal of the dissociation constant of the acid or conjugate acid) of not more than 7.0 acted as a catalyst thereby generation of an active substance between the acid or conjugate acid and a metal oxide.

An orthophtalonitrile having or not having a substituent can be used in the method of the present invention. As concrete examples of the substituent answering the description, such substituents as a halogen atom, alkyl group, aryl group, heterocyclic group, cyano group, hydroxyl group, nitro group, amino group (inclusive of substituted amino group), alkoxyl group, aryloxy group, acylamino group, aminocarbonylamino group, sulfamoylamino group, alkylthio group, arylthio group, sulfonylamino group, carbamoyl group, sulfamoyl group, sulfonyl group, alkoxycarbonyl group, heterocyclic oxy group, azo group, acyloxy group, carbamoyloxy group, silyloxy group, aryloxycarbonyl group, imide group, and heterocyclic thio group, sufinyl group, phosphoryl group, acyl group may be cited.

Preferable substituents exhibit smaller $\sigma_p$ values than $\sigma_m$ values in the Hammett's rule. The substituent exhibiting smaller $\sigma_p$ values than $\sigma_m$ values in the Hammett's rule has no particular limit to impose. As concrete examples of the substituent answering the description, such substituents as a halogen atom, alkyl group, aryl group, heterocyclic group, hydroxyl group, amino group (inclusive of substituted amino group), alkoxyl group, aryloxy group, acylamino group, aminocarbonylamino group, sulfamoylamino group, alkylthio group, arylthio group, alkoxycarbonylamino group, sulfonylamino group, carbamoyl group, sulfamoyl group, heterocyclic oxy group, azo group, acyloxy group, carbamoyloxy group, silyloxy group, imide group, and heterocyclic thio group may be cited. The orthophthalonitrile compound is allowed to incorporate one or more kinds thereof, and any integral number of the pertinent substituents in the range of 1–4.

Preferably, the phthalonitrile compound which is having a substituent exhibiting smaller $\sigma_p$ values than $\sigma_m$ values in the Hammett's rule has one to four substituents which may be the same or different, each representing a halogen atom or at least one member selected from the class consisting of $-R^1$, $-NHR^2$, $-NR^3R^4$, $-OR^5$, and $-SR^6$, wherein $R^1-R^6$ independently stand for an optionally substituted alkyl group or aryl group.

The term "halogen" as used herein refers to fluorine, chlorine, bromine, or iodine. Among other halogens mentioned here, chlorine and fluorine prove to be preferable and fluorine most preferable.

The alkyl groups which may be optionally had the substituents represented by $R^1$–$R^6$ mentioned above include linear, branched, or cyclic alkyl groups of 1–20 carbon atoms, and the same alkyl groups optionally had such substituents as a halogen atom, alkoxyl, nitro, amino, alkoxycarbonyl, halogenated alkoxyl group, halogenated alkyl group, halogenated alkoxycarbonyl, and aryl group, preferably linear, branched, or cyclic alkyl groups of 1–8 carbon atoms, and the same alkyl groups optionally had such substituents as a halogen atom, alkoxyl, nitro, amino, alkoxycarbonyl, halogenated alkoxycarbonyl, and aryl group. As concrete examples of the alkyl group mentioned above, methyl group, ethyl group, n-propyl group, isopropyl group, n-butyl group, tert-butyl group, n-pentyl group, n-hexyl group, cyclohexyl group, n-octyl group, 2-ethylhexyl group, n-decyl group, lauryl group, and stearyl group, and the same alkyl groups had such substituents as halogen atom, alkyl group, alkoxyl group, halogenated alkyl group, halogenated alkoxy group, nitro group, amino group, alkylamino group, alkoxycarbonyl group, halogenated alkoxycarbonyl group, and aryl group.

Particularly desirably, the atoms of which the alkyl group but hydro atom is formed have such radii as total not less than 3.0 Å. For the main atoms involved herein, the following numerals (in Å) are used to indicate relevant atomic radiuses; carbon=0.77, oxygen=0.74, nitrogen=0.74, fluorine=0.72, chlorine=0.99, bromine=1.14, silicon=1.17, phosphorus=1.10, and sulfur=1.04. The fact that the total of radii exceeds 3.0 Å is advantageous in respect that the phthalocyanine compound having this total manifests practically significant solubility in solvents.

As concrete examples of the aryl group which is optionally had substituents represented by $R^1$–$R^6$ mentioned above, aryl groups such as phenyl group, tolyl group, xylyl group, mesityl group, cumenyl group, biphenylyl group, naphthyl group, anthryl group, and phenanthryl group, and the same aryl groups had such substituents as a halogen atom, alkyl group, alkoxyl group, halogenated alkyl group, halogenated alkoxyl group, nitro group, amino group, alkylamino group, alkoxycarbonyl group, and halogenated alkoxycarbonyl group and aryl group may be cited. Among them, the same aryl groups had such substituents as a halogen atom, halogenated alkyl group and halogenated alkoxycarbonyl group may be more preferable, the same aryl groups had such substituents as a alkoxycarbonyl group and aryl group may be particularly preferable. As concrete examples of the halogen atoms which are usable as substituents in the alkyl groups or aryl groups mentioned above, fluorine atom, chlorine atom, bromine atom, and iodine atom may be cited. Among other halogen atoms mentioned above, bromine atom proves to be particularly advantageous.

The alkyl groups which can be used as substituents in the aryl groups mentioned above are linear, branched, or cyclic alkyl groups of 1–20 carbon atoms, preferably linear, branched, or cyclic alkyl groups of 1–8 carbon atoms. As concrete examples of these alkyl groups, methyl group, ethyl group, n-propyl group, isopropyl group, cyclopropyl group, n-butyl group, isobutyl group, sec-butyl group, tert-butyl group, linear or branched pentyl groups such as n-pentyl group, linear or branched hexyl groups such as n-hexyl group, cyclohexyl group, linear or branched heptyl groups, linear or branched octyl groups such as n-octyl group, linear or branched nonyl groups such as 2-ethylhexyl group, linear or branched decyl groups such as n-decyl group, linear or branched undecyl groups, linear or branched dodecyl groups, lauryl group, stearyl group, and the same alkyl groups had such substituents as halogen atom, alkyl group, alkoxyl group, halogenated alkyl group, halogenated alkoxyl group, nitro group, amino group, alkylamino group, alkoxycarbonyl group, halogenated alkoxycarbonyl group, and aryl group may be cited.

The alkoxyl groups which are usable as substituents for the alkyl groups or aryl groups are linear, branched, or cyclic alkoxyl groups of 1–20 carbon atoms, preferably linear, branched, or cyclic alkoxyl groups of 1–8 carbon atoms. As concrete examples of these alkoxyl groups, methoxy group, ethoxy group, n-propyloxy group, isopropyloxy group, n-butoxy group, isobutoxy group, sec-butoxy group, tert-butoxy group, linear or branched pentyloxy groups such as n-pentyloxy group, linear or branched hexyloxy groups such as n-hexyloxy group, cyclohexyloxy group, linear or branched heptyloxy groups such as n-heptyloxy group, linear or branched octyloxy group such as n-octyloxy group, 2-ethylhexyloxy group, linear or branched nonyloxy groups such as n-nonyloxy group, linear or branched docyloxy groups such as n-decyloxy group, linear or branched undecyloxy groups, linear or branched dodecyloxy groups, methoxyethoxy group, ethoxyethoxy group, 3',6'-oxaheptyloxy group, 3',6'-oxaoctyloxy group, 3',6',9'-oxadecyloxy group, 3', 6', 9',12'-oxatridecyloxy group, methoxy-propyloxy group, ethoxypropyloxy group, 4',8'-oxanonyloxy group, and 4',8'-oxadecyloxy group may be cited.

The halogenated alkyl groups which can be used as substituents for the alkyl groups and aryl groups mentioned above are partially halogenated linear, branched, or cyclic alkyl groups of 1–20 carbon atoms, preferably partially halogenated linear, branched, or cyclic alkyl groups of 1–8 carbon atoms, and particularly preferably partially brominated linear, branched, or cyclic alkyl groups of 1–8 carbon atoms. As concrete examples of these halogenated aryl groups, chloromethyl group, bromomethyl group, dichloromethyl group, dibromomethyl group, trichloromethyl group, tribromomethyl group, 1-chloroethyl group, 1-bromoethyl group, 2-chloroethyl group, 2-bromoethyl group, 1,2-dichloroethyl group, 1,2-dibromoethyl group, 1,1-dichloroethyl group, 1,1-dibromoethyl group, 2,2-dichloroethyl group, 2,2-dibromoethyl group, 1,1,2-trichloroethyl group, 1,1,2-tribromoethyl group, 1,2,2-trichloro-ethyl group, 1,2,2-tribromoethyl group, 1-chloropropyl group, 1-bromopropyl group, 2-chloro-1-propyl group, 2-bromo-1-propyl group, 3-chloro-1-propyl group, 3-bromo-1-propyl group, 1-chloro-2-propyl group, 1-bromo-2-propyl group, 2,3-dichloro-1-propyl group, 2,3-dibromo-1-propyl group, 1,3-dichloro-2-propyl group, 1,3-dibromo-2-propyl group, 4-chloro-1-butyl group, 4-bromo-1-butyl group, 1-chloro-1-butyl group, 1-bromo-1-butyl group, 1-chloro-2-butyl group, 1-bromo-2-butyl group, 2-chloro-1-butyl group, 2-bromo-1-butyl group, 1,3-dichloro-2-butyl group, 1,3-dibromo-2-butyl group, 1,4-dichloro-2-butyl group, 1,4-dibromo-2-butyl group, 5-chloro-1-pentyl group, 5-bromo-1-pentyl group, 1-chloro-1-pentyl group, 1-bromo-1-pentyl group, 6-chloro-1-hexyl group, 6-bromo-1-hexyl group, 1-chloro-1-hexyl group, 1-bromo-1-hexyl group, 7-chloro-1-heptyl group, 7-bromo-1-heptyl group, 1-chloro-1-heptyl group, 1-bromo-1-heptyl group, 8-chloro-1-octyl group, 8-bromo-1-octyl group, 1-chloro-1-octyl group, 1-bromo-1-octyl group, 9-chloro-1-nonyl group, 9-bromo-1-nonyl group, 1-chloro-1-nonyl group, 1-bromo-1-nonyl group, 10-chloro-1-decyl group, 10-bromo-1-decyl group, 1-brro-1-decyl group, 1-bromo-1-decyl group, 11-chloro-1-undecyl group, 11-bromo-1- undecyl group, 1-chloro-1-undecyl group, 1-bromo-1-undecyl group, 12-chloro-1-dodecyl group, 12-bromo-1-dodecyl group, 1-chloro-1-dodecyl group, and 1-bromo-1-dodecyl group may be cited.

The halogenated alkoxyl groups which can be used as substituents for the alkyl groups or aryl groups mentioned above are partially halogenated linear, branched, or cyclic alkoxyl groups of 1–20 carbon atoms, preferably partially halogenated linear, branched, or cyclic alkoxyl groups of 1–8 carbon atoms, and particularly preferably partially brominated linear, branched, or cyclic alkoxyl groups of 1–8 carbon atoms. As concrete examples of these halogenated alkoxyl groups, chloro-methoxy group, bromomethoxy group, dichloromethoxy group, dibromomethoxy group, trichloromethoxy group, tribromomethoxy group, 1-chloroethoxy group, 1-bromoethoxy group, 2-chloroethoxy group, 2-bromoethoxy group, 1,2-dichloroethoxy group, 1,2-dibromoethoxy group, 1,1-dichloroethoxy group, 1,1-dibromoethoxy group, 2,2-dichloroethoxy group, 2,2-dibromoethoxy group, 1,1,2-trichloroethoxy group, 1,1,2-tribromoethoxy group, 1,2,2-trichloroethoxy group, 1,2,2-tribromoethoxy group, 1-chloro-propoxy group, 1-bromopropoxy group, 2-chloro-1-propoxy group, 2-bromo-1-propoxy group, 3-chloro-1-propoxy group, 3-bromo-1-propoxy group, 1-chloro-2-propoxy group, 1-bromo-2-propoxy group, 2,3-dichloro-1-propoxy group, 2,3-dibromo-1-propoxy group, 1,3-dichloro-2-propoxy group, 1,3-dibromo-2-propoxy group, 4-chloro-1-butoxy group, 4-bromo-1-butoxy group, 1-chloro-1-butoxy group, 1-bromo-1-butoxy group, 1-chloro-2-butoxy group, 1-bromo-2-butoxy group, 2-chloro-1-butoxy group, 2-bromo-1-butoxy group, 1,4-dichloro-2-butoxy group, 1,4-dibromo-2-butoxy group, 5-chloro-1-pentyloxy group, 5-bromo-1-pentyloxy group, 1-chloro-1-pentyloxy group, 1-bromo-1-pentyloxy group, 6-chloro-1-hexyloxy group, 6-bromo-1-hexyloxy group, 1-chloro-1-hexyloxy group, 1-bromo-1-hexyloxy group, 7-chloro-1-heptyloxy group, 7-bromo-1-heptyloxy group, 1-chloro-1-heptyloxy group, 1-bromo-1-heptyloxy group, 8-chloro-1-octyloxy group, 8-bromo-1-octyloxy group, 1-chloro-1-octyloxy group, 1-bromo-1-octyloxy group, 9-chloro-1-nonyloxy group, 9-bromo-1-nonyloxy group, 1-chloro-1-nonyloxy group, 1-bromo-1-nonyloxy group, 10-chloro-1-decyloxy group, 10-bromo-1-decyloxy group, 1-chloro-1-decyloxy group, 1-bromo-1-decyloxy group, 11-chloro-1-undecyloxy group, 11-bromo-1-undecyloxy group, 1-chloro-1-undecyloxy group, 1-bromo-1-undecyloxy group, 12-chloro-1-decyloxy group, 12-bromo-1-dodecyloxy group, $^1$-chloro-1-dodecyloxy group, 11-bromo-1-dodecyloxy group, chloromethoxyethoxy group, bromomethoxyethoxy group, 1-chloroethoxyethoxy group, 1-bromoethoxyethoxy group, 1-chloro-3',6'-oxaheptyloxy group, 1-bromo-3',6'-oxaheptyloxy group, 1-chloro, 3',6'-oxaoctyloxy group, 1-bromo-3',6'-oxaoctyloxy group, 1-chloro-3',6',9'-oxadecyloxy group, 1-bromo-3',6',9'-oxadecyloxy group, 1-chloro-3',6',9',12'-oxatridecyloxy group, 1-bromo-3',6',9',12'-oxatridecyloxy group, chloromethoxypropoxy group, bromomethoxypropoxy group, 1-chloro-ethoxypropoxy group, 1-bromoethoxypropoxy group, 1-chloro-4',8'-oxanonyloxy group, 1-bromo-4',8'-oxanonyloxy group, 1-chloro-4',8'-oxadecyloxy group, and 1-bromo-4',8'-oxadecyloxy group may be cited.

The alkylamino groups which can be used as substituents for the aryl groups mentioned above are linear, branched, or cyclic alkylamino groups of 1–20 carbon atoms, preferably linear, branched, or cyclic alkylamino groups of 1–8 carbon atoms. As concrete examples of these alkylamino groups, methylamino group, ethylamino group, n-propylamino group, isopropylamino group, n-butylamino group, tert-butylamino group, n-pentylamino group, n-hexylamino group, cyclohexylamino group, n-octylamino group, 2-ethylhexylamino group, and n-decylamino group may be cited.

The alkoxycarbonyl groups which can be used as substituents for the alkyl groups or aryl groups mentioned above are alkoxycarbonyl groups of 1–8 carbon atoms, preferably 1–5 carbon atoms, optionally containing hetero atoms in the alkyl group moiety of the alkoxyl group thereof or cyclic alkoxycarbonyl groups of 3–8 carbon atoms, preferably 5–8 carbon atoms, optionally containing hetero atoms therein. As concrete examples of these alkoxycarbonyl groups, methoxycarbonyl group, ethoxy-carbonyl group, propoxycarbonyl group, isopropoxycarbonyl group, n-butoxycarbonyl group, isobutoxycarbonyl group, sec-butoxy-carbonyl group, tert-butoxycarbonyl group, linear or branched pentyloxycarbonyl group, n-hexyloxycarbonyl group, linear or branched hexyloxycarbonyl groups such as 2-ethylhexyl-oxycarbonyl group, cyclohexyloxycarbonyl group, linear or branched heptyloxy-carbonyl group, linear or branched octyloxycarbonyl group, linear or branched nonyloxycarbonyl group, linear or branched decyloxy-carbonyl group, linear or branched undecyloxycarbonyl group, linear or branched dodecyloxycarbonyl group, methoxyethoxycarbonyl group, cyclohexanemethoxycarbonyl group, cyclohexaneethoxycarbonyl group, 3-chlorohexyl-1-propoxycarbonyl group, tert-butylcyclohexyloxycarbonyl group, phenoxycarbonyl group, 4-methylphenoxycarbonyl group, 4-chlorophenoxycarbonyl group, 4-cyclohexylphenoxycarbonyl group, 4-phenylphenoxycarbonyl group, 2-fluorophenoxycarbonyl group, 4-ethoxyphenoxycarbonyl group, ethoxyethoxycarbonyl group, butoxyethoxycarbonyl group, diethyl-aminoethoxycarbonyl group, methylethioethoxycarbonyl group, 3',6'-oxaheptyloxycarbonyl group, 3',6'-oxaoctyloxycarbonyl group, 3',6',9'-oxadecyloxycarbonyl group, 3',6',9',12'-oxatridecyloxycarbonyl group, methoxypropyloxycarbonyl group, ethoxy-propyloxycarbonyl group, 4',8'-oxanonyloxycarbonyl group, 4',8'-oxadecyloxycarbonyl group, 4',8',12'-oxatridecyloxycarbonyl group, tetrahydrofurfuryloxycarbonyl group, pyranoxycarbonyl group, piperidinoxycarbonyl group, piperidinoethoxycarbonyl group, tetrahydropyrroloxycarbonyl group, tetrahydropyranmethoxy-carbonyl group, tetrahydrothiophenoxycarbonyl group, cyclohexyl-oxycarbonyl group, benzyloxycarbonyl group, phenethyloxycarbonyl group, 3-phenyl-1-propoxycarbonyl group, 4-phenyl-1-butoxycarbonyl group, 5-phenyl-1-pentoxycarbonyl group, 6-phenyl-1-hexyloxycarbonyl group, 2-tetrahydrofuranoxycarbonyl group, 4-tetrahydropyranoxycarbonyl group, 2-pyrrolidinoxycarbonyl group, 2-piperidinoxycarbonyl group, 2-tetrahydrothiophenoxycarbonyl group, tetrahydrofurfuryloxycarbonyl group, 4-tetrahydropyranoxycarbonyl group, 2-morpholinoethoxycarbonyl group, 2-pyrrolidinoethoxycarbonyl group, and 2-piperadinoethoxycarbonyl group may be cited.

The halogenated alkoxycarbonyl groups which can be used as substituents for the alkyl groups or aryl groups mentioned above are partially halogenated alkoxycarbonyl groups of 1–8 carbon atoms, preferably 1–5 carbon atoms, optionally containing hetero atoms in the alkyl group moiety of the alkoxyl group thereof or partially halogenated cyclic alkoxycarbonyl groups of 3–8 carbon atoms, preferably 5–8 carbon atoms, optionally containing hetero atoms therein. As concrete examples of these halogenated alkoxycarbonyl groups, chloromethoxycarbonyl group, bromomethoxycarbonyl group, 2-chloroethoxycarbonyl group, 2-bromoethoxycarbonyl group, 3-chloro-1-propoxycarbonyl group, 3-bromo-1-propoxycarbonyl group, 2-chloro-1-propoxycarbonyl group, 2-bromo-1-propoxycarbonyl group, 1-chloro-2-propoxycarbonyl group, 1-bromo-2-propoxycarbonyl group, 2,3-dichloro-1-propoxycarbonyl group, 2,3-dibromo-1-propoxycarbonyl group, 1,3-dichloro-2-propoxycarbonyl group, 1,3-dibromo-2-propoxycarbonyl group, 1-chloro-2-butoxycarbonyl group, 1-bromo-2-butoxycarbonyl group, 2-chloro-1-butoxycarbonyl group, 2-bromo-1-butoxycarbonyl group, 4-chloro-1-butoxycarbonyl group, 4-bromo-1-butoxycarbonyl group, 1,4-dichloro-2-butoxycarbonyl group, 1,4-dibromo-2-butoxycarbonyl group, 5-chloro-1-pentyloxycarbonyl group, 5-bromo-1-pentyloxycarbonyl group, 6-chloro-1-hexyloxycarbonyl group, 6-bromo-1-hexyloxycarbonyl group, 7-chloro-1-heptyloxycarbonyl group, 7-bromo-1-heptyloxycarbonyl group, 8-chloro-1-octyloxy-carbonyl group, 8-bromo-1-octyloxycarbonyl group, 9-chloro-1-nonyloxycarbonyl group, 9-bromo-1-nonyloxycarbonyl group, 10-chloro-1-decyloxycarbonyl group, 10-bromo-1-decyloxycarbonyl group, 11-chloro-1-undecyloxycarbonyl group, 11-bromo-1-undecyloxycarbonyl group, 12-chloro-1-dodecyloxycarbonyl group, and 12-bromo-1-dodecyloxycarbonyl group may be cited.

The aryl groups which can be used as substituents for the alkyl groups or aryl groups mentioned above are optionally substituted aryl groups. As concrete examples of these aryl groups, phenyl group, o-methylphenyl group, m-methylphenyl group, p-methylphenyl group, o-ethylphenyl group, m-ethylphenyl group, p-ethylphenyl group, o-propylphenyl group, m-propylphenyl group, p-propylphenyl group, o-isopropylphenyl group, m-isopropylphenyl group, p-isopropylphenyl group, o-butylphenyl group, m-butyl-phenyl group, p-butylphenyl group, o-tert-butylphenyl group, m-tert-butylphenyl group, p-tert-butylphenyl group, o-methoxyphenyl group, m-methoxyphenyl group, p-methoxyphenyl group, o-ethoxy-phenyl group, m-ethoxy-phenyl group, p-ethoxy-phenyl group, o-propoxyphenyl group, m-propoxyphenyl group, p-propoxyphenyl group, o-isopropoxyphenyl group, m-isopropoxyphenyl group, p-isopropoxyphenyl group, o-butoxyphenyl group, m-butoxy-phenyl group, p-butoxyphenyl group, 2,6-dimethylphenyl group, 2,6-diethylphenyl group, 2,6-dipropylphenyl group, 2,6-diisopropylphenyl group, 2,6-dibutylphenyl group, 2,6-di-tert-butyl-phenyl group, 2,6-dimethoxyphenyl group, 2,6-diethoxyphenyl group, 2,6-dipropoxyphenyl group, 2,6-diisopropoxyphenyl group, 2,6-dibutoxyphenyl group, 2-fluorophenyl group, 2-chlorophenyl group, 2-bromophenyl group, 2-iodophenyl group, 3-fluorophenylgroup, 3-chlorophenyl group, 3-bromophenyl group, 3-iodophenyl group, 4-fluorophenyl group, 4-chlorophenyl group, 4-bromophenyl group, 4-iodophenyl group, 2,3-difluorophenyl group, 2,3-dichlorophenyl group, 2,4-difluorophenyl group, 2,4-dichloro-phenyl group, 2,4-dibromophenyl group, 2,5-difluorophenyl group, 2,5-dichlorophenyl group, 2,6-difluorophenyl group, 2,6-dichloro-phenyl group, 2,6-dibromophenyl group, 3,4-difluorophenyl group, 3,4-dichlorophenyl group, 3,5-difluorophenyl group, 3,5-dichloro-phenyl group, 2,3,4-trifluorophenyl group, 2,3,4-trichlorophenyl group, 2,3,5-trifluorophenyl group, 2,3,5-trichlorophenyl group, 2,3,6-trifluorophenyl group, 2,3,6-trichlorophenyl group, 2,4,6-trifluorophenyl group, 2,4,6-trichlorophenyl group, 2,4,6-tribromophenyl group, 2,4,6-triiodophenyl group, 2,3,5,6-tetra-fluorophenyl group, pentafluorophenyl group, and pentachloro-phenyl group may be cited.

The substituents in the substituted alkyl groups or aryl groups may be in one same kind or in two or more different kinds.

When the benzene ring of the orthophthalonitrile compound has introduced one to three substituents which are represented by —$R^1$, —$NHR^2$, —$NR^3R^4$, —$OR^5$, and —$SR^6$ mentioned above, halogen atoms are preferred to occupy the remaining positions of the ring. Among other halogen atoms mentioned above, fluorine and chlorine atom prove to be preferable and fluorine atom to be particularly preferable.

As concrete examples of the orthophthalonitrile compound as described above, orthophthalonitrile, 3-nitrophthalonitrile, 3-(2-ethoxy)carbonylphthalonitrile, 3-trifluoromethylphthalonitrile, tetrafluorophthalonitrile, 3,4,5-trifluorophthalonitrile, 3,4,6-trifluorophthalonitrile, 3,4-difluorophthalonitrile, 3,5-difluorophthalonitrile, 3,6-difluorophthalonitrile, 4,5-difluorophthalonitrile, 3-fluorophthalonitrile, 4-fluorophthalonitrile, tetrachlorophthalonitrile, 3,4,5-trichlorophthalonitrile, 3-chloro-4-fluorophthalonitrile, 4-tert-butylphthalonitrile, 4-hydroxyphthalonitrile, 4-aminophthalonitrile, 3,5,6-trifluoro-4-methylaminophthalonitrile, 4-ethylamino-3,5,6-trifluorophthalonitrile, 4-butylamino-3,5,6-trifluorophthalonitrile, 4-anilino-3,5,6-trifluorophthalonitrile, 3,5,6-trifluoro-4-(o-toluidino)-phthalonitrile, 3,5,6-trifluoro-4-(p-toluidino)phthalonitrile, 3,5,6-trifluoro-4-(2,4-xylidino)phthalonitrile, 3,5,6-trifluoro-4-(2,6-xylidino)phthalonitrile, 4-(o-chloroanilino)-3,5,6-trifluorophthalonitrile, 4-(p-chloroanilino)-3,5,6-trifluoro-phthalonitrile, 4-(2,4-dichloroanilino)-3,5,6-trifluorophthalonitrile, 4-(2,6-dichloroanilino)-3,5,6-trifluorophthalonitrile, 4-(o-fluoroanilino)-3,5,6-trifluorophthalonitrile, 4-(p-fluoro-anilino)-3,5,6-trifluorophthalonitrile, 4-(2,3,5,6-tetrafluoro-anilino)-3,5,6-trifluorophthalonitrile, 3,5,6-trifluoro-4-methoxyphthalonitrile, 4-ethoxy-3,5,6-trifluorophthalonitrile, 4-butoxy-3,5,6-trifluorophthalonitrile, 3,5,6-trifluoro-4-phenoxy-phthalonitrile, 3,5,6-trifluoro-4-(o-methylphenoxy)phthalonitrile, 3,5,6-trifluoro-4-(p-methylphenoxy)phthalonitrile, 3,5,6-trichloro-4-(p-methylphenoxy)phthalonitrile, 3,5,6-trifluoro-4-(2,4-dimethylphenoxy)phthalonitrile, 3,5,6-trifluoro-4-(2,6-dimethylphenoxy)phthalonitrile, 4-(o-chloro-phenoxy)-3,5,6-trifluorophthalonitrile, 4-(p-chlorophenoxy)-3,5,6-trifluorophthalonitrile, 4-(2,4-dichorophenoxy)-3,5,6-trifluorophthalonitrile, 4-(2,6-dichlorophenoxy)-3,5,6-trifluoro-phthalonitrile, 4-(o-fluorophenoxy)-3,5,6tritrifluorophthalonitrile, 4-(p-fluorophenoxy)-3,5,6-trifluorophthalonitrile, 4-(2,3,5,6-tetrafluorophenoxy)-3,5,6-trifluorophthalonitrile, 3,5,6-trifluoro-4-(2,6-dimethoxyphenoxy)phthalonitrile, 3,5,6-trifluoro-4-(2-methyl-6-methoxyethoxycarbonylphenoxy)phthalonitrile, 3,5,6-trifluoro-4-(2-methoxy-6-methoxyethoxycarbonylphenoxy)phthalonitrile, 3,5,6-trifluoro-4-(2-ethoxy-6-methoxy-ethoxycarbonylphenoxy) phthalonitrile, 3,5,6-trifluoro-4-(2-methyl-6-tetrahydrofurfuryloxycarbonylphenoxy)phthalonitrile, 3,5,6-trifluoro-4-(2-methyl-6-methoxyethoxyethoxycarbonylphenoxy)phthalonitrile, 3,5,6-trifluoro-4-(2,6-dimethoxyethoxy-carbonylphenoxy) phthalonitrile, 3,5,6-trifluoro-4-(2-methoxyethoxycarbonyl-6-phenylphenoxy)phthalonitrile, 3,5,6-trifluoro-4-(2-methoxyethoxyethoxycarbonyl-6-phenylphenoxy)phthalonitrile, 3,5,6-trifluoro-4-(2-tetrahydrofurfuryloxycarbonyl-6-phenyl-phenoxy) phthalonitrile, 3,5,6-trifluoro-4-(2-(2-propoxycarbonyl)-6-phenylphenoxy)phthalonitrile, 3,5,6-trifluoro-4-(2-(3-pentoxy-carbonyl)-6-phenylphenoxy)phthalonitrile, 3,5,6-trichloro-4-(2-(2-methoxyethoxy)carbonyl-6-methylphenoxy)phthalonitrile, 3,5,6-trifluoro-4-(2-(2,4-dimethyl-3-pentoxycarbonyl)-6-phenylphenoxy)-phthalonitrile, 3,5,6-trifluoro-4-(2-(2,6-dimethyl-4-heptyloxy-carbonyl)-6-phenylphenoxy)phthalonitrile, 4-(2-(1,3-dibromo-2-propoxycarbonyl)-6-phenyl)phenoxy-3,5,6-trifluorophthalonitrile, 4-(2-bromoethoxycarbonyl-6-phenyl)phenoxy-3,5,6-trifluorophthalo-nitrile, 4-(2,4-di(6-bromohexyloxycarbonyl)-6-phenyl)phenoxy-3,5,6-trifluorophthalonitrile, 4-(2-(1-bromo-2-propoxycarbonyl)-6-phenyl)phenoxy-3,5,6-trifluorophthalonitrile, 4-(2-(1,4-dibromo-2-butoxycarbonyl)-6-phenyl)phenoxy-3,5,6-trifluoro-phthalonitrile, 4-(6-(bromophenyl)-2-(2-propoxycarbonyl))phenoxy-3,5,6-trifluorophthalonitrile, 4-(bromo-2-(2-propoxycarbonyl)-6-phenyl)phenoxy-3,5,6-trifluorophthalonitrile, 3,6-difluoro-4,5-bismethylthiophthalonitrile, 3,6-difluoro-4,5-bismethylthio-phthalonitrile, 3,6-difluoro-4,5-bisethylthio-phthalonitrile, 3,6-difluoro-4,5-bisbutylthiophthalonitrile, 3,6-difluoro-4,5-bis(tert-butylthio)phthalonitrile, 3,6-difluoro-4,5-bisphenylthiophthalonitrile, 4,5-bisethylphenylthio-3,6-difluorophthalo-nitrile, 3,6-difluoro-4,5-bispropylphenylthiophthalonitrile, 4,5-bisbutylphenylthio-3,6-difluorophthalonitrile, 3,6-difluoro-4,5-bis(tertbutylphenylthio)phthalonitrile, 3,6-difluoro-4,5-bis(o-tolylthio)phthalonitrile, 3,6-difluoro-4,5-bis(p-tolylthio)-phthalonitrile, 3,6-difluoro-4,5-bis(m-tolylthio)phthalonitrile, 3,6-difluoro-4,5-bis(2,4-xylylthio)phthalonitrile, 3,6-difluoro-4,5-bis(2,3-xylylthio)phthalonitrile, 3,6-difluoro-4,5-bis(2,6-xylylthio)phthalonitrile, 4,5-bis(o-chlorophenylthio)-3,6-difluorophthalonitrile, 4,5-bis(p-chlorophenylthio)-3,6-difluoro-phthalonitrile, 4,5-bis(2,4-dichlorophenylthio)-3,6-difluoro-phthalonitrile, 4, 5-bis (2,6-dichlorophenylthio)-3,6-difluoro-phthalonitrile, 3,6-difluoro-4,5-bis(o-fluorophenylthio)phthalo-nitrile, 3,6-difluoro-4,5-bis(p-fluorophenylthio)phthalonitrile, 3,6-difluoro-4,5-bis(2,3,5,6-tetrafluorophenylthio)phthalo-nitrile, 4-anilino-5-phenylthio-3,6-difluorophthalonitrile, 4-anilino-5-butoxy-3,6-difluorophthalonitrile, 4-butylthio-5-phenoxy-3,6-difluorophthalonitrile, 4-butoxy-5-phenoxy-3,6-difluorophthalonitrile, 4-anilino-5-(o-toluidino)-3,6-difluoro-phthalonitrile, 3-fluoro-4,5,6-triphenoxyphthalonitrile, 3,4,5,6-tetraphenylthiophthalonitrile, 4-phenylthio-3,5,6-trifluorophthalonitrile, 4-(2-ethoxycarbonyl-6-methyl)phenoxy- 3,5,6-trifluorophthalonitrile, 4-(2-phenyl)phenoxy-3,5,6-trifluoro-phthalonitrile, and 4,5-diphenoxy-3,6-difluorophthalonitrile may be cited.

Then, the metal oxide to be used in this invention has no particular limit to impose. As concrete examples of the metal oxide, the oxides of vanadium, titanium, iron, magnesium, nickel, cobalt, copper,silver, palladium, zinc, germanium, tin, silicon and lithium may be cited. As concrete examples of metal oxides, vanadium oxide, vanadium trioxide, vanadium tetraoxide, vanadium pentoxide, titanium dioxide, iron oxide, iron sesquioxide, triiron tetraoxide, manganese oxide, nickel oxide, cobalt oxide, cobalt sesquioxide, cabalt dioxide, copper(I) oxide, copper(II) oxide, copper sesquioxide, palladium oxide, zinc oxide, germanium oxide, germanium dioxide, tin oxide, tin dioxide, silicon oxide, silicon dioxide and lithium oxide may be cited. Among other metal oxides mentioned above, the oxides of metals having a valency of at least 2 prove to be preferable, the oxides of metals having a valency of at least 3 prove such as titanium oxides and vanadium oxides to be more preferable, and vanadium oxides prove to be particularly preferable. As concrete examples of vanadium oxides, vanadium trioxide, vanadium tetroxide, and vanadium pentoxide may be cited. Among other vanadium oxides mentioned above, lower oxides of vanadium prove to be preferable and vanadium trioxide proves to be particularly preferable. The use of the metal oxide in the method of production of this invention brings out the merit of precluding introduction of chlorine atoms into the phthalocyanine skeleton as compared with the conventional method of production of phthalocyanine using a chloride as a metal salt.

The amount of the metal oxide mentioned above to be incorporated relative to the amount of the orthophthalonitrile compound mentioned above is only required to exceed the due stoichiometric amount. The metal oxide, however, is generally incorporated in an amount in the range of 1–2 equivalent weights, preferably in the range of 1.1–1.5 equivalent weights, based on four equivalent weights of the orthophthalonitrile compound mentioned above. If the amount of the metal oxide is less than one equivalent weight based on four equivalent weights of the orthophthalonitrile compound, the relevant reaction will possibly by-produce a metal-less phthalocyanine compound because of stoichiometrically insufficient supply of the metal oxide. Conversely, if the amount exceeds two equivalent weights based on the four equivalent weights of the orthophthalonitrile compound, then the excess supply will be at a disadvantage in increasing the amount of an unaltered metal oxide to the extent of rendering the production of the compound uneconomical and necessitating an extra work of recovering or removing the unaltered metal oxide from the reaction solution during the process of purification.

The method of production according to this invention prefers the relevant reaction to proceed in the presence of a compound forming in the aqueous solution thereof at 25° C. an acid or conjugate acid having a dissociation index pKa (the logarithmic value of the reciprocal of the dissociation constant of the acid or conjugate acid) of not more than 7.0. The expression "having a pKa of not more than 7.0" as used herein is meant to embrace a compound which, during an operation of multi-stage dissociation, registers a pKa of not more than 7.0 at the first stage even when it registers a pKa exceeding 7.0 at the second and subsequent stages. Preferably, the compound registers a pKa of not more than 7.0 at all the stages of dissociation. More preferably, the reaction is carried out in the presence of a compound whose pKa is in the range of (−5.0)–(5.0). This invention has stemmed from the discovery that when the synthesis of a phthalocyanine compound by the reaction of an orthophthalonitrile compound with a metal oxide is carried out in the presence of a compound forming in the aqueous solution thereof at 25° C. an acid or conjugate acid having a dissociation index pKa of not more than 7.0, this compound functions as a highly effective catalyst for the reaction. If the pKa of the compound exceeds 7.0, the excess will be at a disadvantage in preventing the compound from manifesting a sufficient catalytic activity and allowing the reaction for the formation of phthalocyanine to proceed only with difficulty. For use in the present invention, the compound which forms in the aqueous solution thereof at 25° C. an acid or conjugate acid having a dissociation index pKa of not more than 7.0 has no particular limit to impose and it may be an organic compound or an inorganic compound so long as the pKa thereof is not more than 7.0. As concrete examples of the compound which answers this description, acrylic acid, adipic acid, N-acetyl alanine, N-acetyl glycine, azelaic acid, 5'-adenosine triphosphate, 2'-adenosine phosphate, 3'-adenosine phosphate, 5'-adenosin phosphate, o-anisic acid, m-anisic acid, p-anisic acid, aniline, m-aniline-sulfonic acid, p-anilinesulphonic acid, o-aminobenzoic acid, m-aminobenzoic acid, p-aminobenzoic acid, 2-aminopyridine, 3-aminopyridine, benzoic acid, isovalerianic acid, isoquinoline, isonicotinamide, isonicotinic acid, methyl isonicotinate, isobutyric acid, 5'-inosin-phosphoric acid, oxaloacetic acid, octanoic acid, formic acid, valeric acid, quinaldic acid, quinoline, citric acid, glyoxalic acid, glycolic acid, 2-glycerin-phosphoric acid, D-glucose-1-phosphoric acid, glutaric acid, crotonic acid, o-chloroaniline, m-chloroaniline, p-chloroaniline, o-chlorobenzoic acid, m-chlorobenzoic acid, p-chlorobenzoic acid, chloroacetic acid, 2-chloropropionic acid, 3-chloropropionic acid, ciscinnamic acid, trans-cinnamic acid, succinic acid, acetic acid, m-cyanobenzoic acid, p-cyanobenzoic acid, cyanoacetic acid, o-cyanophenol, cyclohexane-carboxylic acid, dichloroacetic acid, 2,6-dimethyl pyridine, oxalic acid, d-tartaric acid, (R,R)-tartaric acid, thiophenol, thenoyl trifluoroacetyl acetone, trichloroacetic acid, trifluoroacetylacetone, o-toluidine, m-toluidine, p-toluidine, p-toluenesulfonic acid, 1-naphthylamine, 2-naphthylamine, 1-naphthoeic acid, 2-naphthoeic acid, o-nitro-aniline, m-nitroaniline, p-nitroaniline, o-nitrobenzoic acid, m-nitrobenzoic acid, p-nitrobenzoic acid, nitroacetic acid, p-nitrophenol, lactic acid, uric acid, barbituric acid, picric acid, vinyl acetic acid, 2,2'-bipyridine, 4,4'-bipyridine, pimelic acid, pyrazine, pyrazole, pyridine, 2,6-pyridine dicarboxylic acid, pyruvic acid, 1,10-phenanthrolin, phenylacetic acid, o-phenylene diamine, phenoxyacetic acid, fumaric acid, 2-furancarboxylic acid, o-fluorobenzoic acid, m-fluorobenzoic acid, p-fluorobenzoic acid, fluoroacetic acid, propionic acid, o-bromobenzoic acid, m-bromobenzoic acid, p-bromobenzoic acid, bromoacetic acid, hexafluoroacetyl acetone, hexanoic acid, hexanoic acid, heptanoic acid, o-benzenedicarboxylic acid, m-benzenedicarboxylic acid, p-benzenedicarboxylic acid, benzimidazole, maleic acid, malonic acid, mandelic acid, 2-methylpyridine, 3-methylpyridine, 4-methylpyridine, o-iodobenzoic acid, m-iodobenzoic acid, p-iodo-benzoic acid, iodoacetic acid, butyric acid, malic acid, levulinic acid, L-ascorbic acid, asparagine, aspartic acid, adenine, adenosine, 5'-adenosine diphosphate, histamine, 2-(2-aminoethyl) pyridine, 2-aminoethyl phosphoric acid, o-aminophenol, 4-aminobutyric acid, L-alanyl-L-alanine, L-alanyl- glycylglycyl glycin, L-alanylglycyl glycin, β-alanylglycyl glycin, L-alanyl glycin, β-alanylglycin, L-carnosine, L-alanyl-L-phenyl alanine, β-alanine, arginine, isoleucine, inosine, 2-indole carboxylic acid, oxine, ornithine, xanthosine, 2-quinoline carboxylic acid, guanine, guanosine, glycyl-L-alanine, glycyl-β-alanine, glycylglycyl-L-alanine, glycylglycylglycylglycine, glycylglycylglycyl-L-histidine, glycylglycylglycine, glycyl-glycyl-L-histidine, glycylglycine, glycyl-DL-histidylglycine, glycyl-L-histidine, glycyl-L-leusine, glycine, y-L-glutamyl-L-cysteinyl glycine, glutamine, glutamic acid, salicylic acid, sarcosylglycine, L-2,4-diaminobutyric acid, diethylene triamine, cysteine, cytidine, cytosine, citrulline, 3,4-dihydroxyphenyl alanine, N,N-dimethyl glycine, penicillamine, serine, thio-glycolic acid, thyrosine, triethylene tetramine, tryptophan, threonine, nicotinamide, nicotinic acid, DL-norleucine, valine, L-histidylglycine, histidine, m-hydroxybenzoic acid, p-hydroxy-benzoic acid, 4-hydroxyproline, piperazine, hypoxanthine, pyridoxal, pyridoxine, L-phenylalanyl glycine, phenyl alanine, purine, L-prolylglycine, proline, methionine, 3-methylpyrazole, 4-methyl pyrazole, mercaptoacetic acid, lysine, riboflavin, L-leucyl-L-thyrosine, leucine, methane sulfonic acid, ethane sulfonic acid, 1,2-ethane disulfonic acid, trifluoromethane sulfonic acid, 3-hydroxypropane sulfonic acid, 1,3-propane disulfonic acid, heptadecafluorooctane sulfonic acid, benzene sulfonic acid, p-phenol sulfonic acid, 2-nitrobenzene sulfonic acid, 3-nitrobenzene sulfonic acid, 4-nitrobenzene sulfonic acid, 4-chlorobenzene sulfonic acid, 2,4-dinitrobenzene sulfonic acid, 2,5-dichlorobenzene sulfonic acid, 2,4,5-trichlorobenzene sulfonic acid, picryl sulfonic acid, 5-sulfosalicylic acid, 4-nitrotoluene-2-sulfonic acid, 4-sulfophthalic acid, 4-ethyl-benzene sulfonic acid, m-xylene-4-sulfonic acid, p-xylene-2-sulfonic acid, mesitylene sulfonic acid, dodecylbenzene sulfonic acid, 2-naphthalene sulfonic acid, pyridine-3-sulfonic acid, 2,5-dichlorosulfanylic acid, 4-chloroaniline-3-sulfonic acid, 2-amino-4-chlorophenol-6-sulfonic acid, 3-nitroaniline-4-sulfonic acid, 2-aminobenzene sulfonic acid, 3-aminobenzene sulfonic acid, 4-aminobenzene sulfonic acid, 2-aminophenol-4-sulfonic acid, 4-amino-2-chlorotoluene-5-sulfonic acid, 5-amino-2-chlorotoluene-4-sulfonic acid, 2(2-pyridyl)ethane sulfonic acid, 2(4-pyridyl) ethane sulfonic acid, m-toluidine-4-sulfonic acid, p-toluidine-2-sulfonic acid, o-anisidine-5-sulfonic acid, p-anisidine-2-sulfonic acid, p-anisidine-3-sulfonic acid, 2-acryl-amide-2-methylpropane sulfonic acid, 3-cyclohexylaminopropane sulfonic acid, 8-anilino-1-naphthalene sulfonic acid, hydrochloric acid, nitric acid, sulfuric acid, phosphoric acid, and phosphinic acid may be cited. Among other compounds mentioned above, the organic compounds prove to be preferable. The organic compounds are advantageous where the production of phthalocyanine is performed in an organic solvent because they exhibit higher solubility in the organic solvent and they promote the reaction more effectively than the inorganic compounds. Among other organic compounds, organic acids are preferred and organic sulfonic acid compounds are more preferable. Among other organic sulfonic acid compounds, methane sulfonic acid, ethane sulfonic acid, 1,2-ethane disulfonic acid, trifluoromethane sulfonic acid, 3-hydroxypropane sulfonic acid, 1,3-propane disulfonic acid, heptadecafluorooctane sulfonic acid, benzene sulfonic acid, p-phenol sulfonic acid, p-toluene sulfonic acid, 2-nitrobenzene sulfonic acid, 3-nitrobenzene sulfonic acid, 4-nitrobenzene sulfonic acid, 4-chlorobenzene sulfonic acid, 2,4-dinitrobenzene sulfonic acid, 2,5-dichlorobenzene sulfonic acid, 2,4,5-trichlorobenzene sulfonic acid, picryl sulfonic acid, 5-sulfosalicylic acid, 4-nitrotoluene-2-sulfonic acid, 4-sulfophthalic acid, 4-ethylbenzene sulfonic acid, m-xylene-4-sulfonic acid, p-xylene-2-sulfonic acid, mesitylene sulfonic acid, dodecylbenzene sulfonic acid, and 2-naphthalene sulfonic acid prove to be preferable and p-toluene sulfonic acid proves to be particularly preferable to easy obtain for industrial use. The amount of these compounds to be used in the reaction system is not changed before and after the reaction because it serves as a catalyst for the reaction and, therefore, takes no part in the reaction from the stoichiometric point of view. When the reaction is carried out batchwise, for example, the compound used in an amount in the range of 0.05–5 mol %, based on the amount of an orthophthalonitrile functions fully satisfactorily as a catalyst.

The method for the production of a phthalocyanine compound according to this invention requires the reaction of an ortho-phthalonitrile compound and a metal oxide mentioned above to proceed in the presence of a compound having a pKa value of not more than 7.0 as described above. In the reaction conditions involved herein, the reaction temperature is in the range of 30–250° C., preferably 80–200° C. If the reaction temperature is less than 80° C., the catalytic activity of the compound will be degraded to the extent of conspicuously lowering the reaction velocity and notably prolonging the time required for the synthesis and rendering the production uneconomical. If the temperature of the synthesis exceeds 200° C., the excess will bring about a notable addition to the amount of a by-product.

In the method for the production of the present invention can use a method that the metal oxides and the compound having a pKa value of not more than 7.0 as described are mixed in advance, then orthophthalonitrile is added to the mixture for reaction starts. The reaction can get to raise a progress speed for generation of active substances prior to addition of orthophthalonitrile.

In the method for the production of a phthalocyanine compound according to this invention, though the reaction of the orthophthalonitrile compound with the metal oxide mentioned above in the presence of a compound having the pKa value of not more than 7.0 may be carried out without using a solvent, it is preferred to use an organic solvent. The organic solvent is only required to be devoid of reactivity with the starting raw materials. As concrete examples of the organic solvent which fulfills this requirement, nitrogen compound type solvents such as nitromethane, nitroethane, nitrobenzene, triethylamine, tri-n-butylamine, N,N-dimethyl formamide, N-methyl-2-pyridinone, N,N-dimethyl acetophenone, acetonitrile, and benzonitrile, hydrocarbon type solvents such as benzene, toluene, xylene, naphthalene, and 1-methylnaphthalene, halogenated hydrocarbon type solvents such as monochlorobenzene, dichlorobenzene, trichlorobenzene, and 1-chloronaphthalene, alcohol type solvents such as n-octanol and ethylene glycol, and sulfur compound type solvents such as dimethyl sulfoxide and sulforan may be cited. Among other organic solvents mentioned above, nitrogen compound type solvents, hydrocarbon type solvents, and halogenated hydrocarbon type solvents prove to be preferable, nitrogen compound type solvents prove to be particularly preferable for raising a catalyst activity of the compound having the pKa value of not more than 7.0 and generation speed of active substances, and benzonitrile proves to be especially preferable.

In the method for the production of the present invention chlorine or fluorine may be generated at the manufacture progress when chloride atom or fluoro atom are used to the method of the phthalocyanine. These kinds of gas may raise up the issue of equipment cauterization and the like because of generated gas volume. Oxides, hydroxide and carbonate of alkali-earth metal are preferable to trap these kinds of gas, carbonate of alkali-earth metal is more preferable.

Though the method of production described above is capable of synthesizing a phthalocyanine compound aimed at, it is preferred to allow synthesis of such phthalocyanine compounds as manifest outstanding effects in optical recording media having an absorption in a near infrared zone and using a semiconductor laser, liquid crystal display devices, near infrared absorption dyes, near infrared sensitizers, photothermal conversing agents for thermal transfer, near infrared absorption materials such as PDP grade near infrared absorption filters, color separation filters, liquid crystal display color filters, optical color filters, plasma display grade color filters, selective absorption filters for color braun tubes, color toners, ink jet type inks, agents for intercepting heat rays, and heat storing fibers. The center metals for such phthalocyanine compounds impose no restriction particularly but require only to be selected from among metals and oxidized metals. They are preferred to be divalent metal atoms or oxy metals containing tetravalent metals. As concrete examples of these divalent metal atoms or oxy metals containing tetravalent metals, divalent metal atoms such as iron, magnesium, nickel, cobalt, copper, palladium, and zinc and oxy metals containing tetravalent metals such as titanyl and vanadyl. Among other center metals mentioned above, oxy metals containing tetravalent metals prove to be more preferable, vanadyl prove to be particularly preferable.

As concrete examples of the phthalocyanine compound which is synthesized by the method of production according to this invention, the following compounds may be cited.

Tetra-tert-butyl copper phthalocyanine,
Copper phthalocyanine,
Titanyl phthalocyanine,
Tetrakisnitronickelphthalocyanine,
Tetrakis(n-butoxy)cobaltphthalocyanine,
Tetrakis(methoxycarbonyl)vanadylphthalocyanine,
octakisbutylthiooctaphthalovanadylphthalocyanine,
Tetrabuthoxydodecafluorozincphthalocyanine.

Among them a phthalocyaneine compound having to the extent of bulky substituent prove to be preferable.

As these concrete examples, a compound represented the following formula (1)

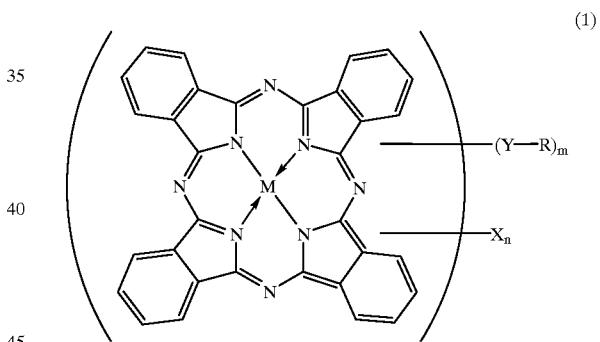

[wherein X and Y-R are represented substituents where bind any position of 16 displaceable on benzene nucleus of phthalocyanine skeleton, M is represented metal, metal oxides or halogenated metal, Y is represented any of one selected from the group consisting of 0, S and NH, R is represented alkyl group or aryl group possessable of substituent, X is represented hydrogen atom or halogen atom( preferably halogen atom), m is an integer of 0–16 ( preferably 4–16), n is an integer of 0–16 (preferably 0–12 ), m+n is an integer of not more than 16, and the total sum of atom radiuses which atoms but halogen atom is included in R is not less than 4.0 Å] is cited.

As concrete examples,
Hexadecachlorovanad phthalocyanine,
Hexadecachlorovanadyl phthalocyanine,
Tetrakis(2-phenyl-6-(2-propyl)phenoxy)dodecafluoro zinc phthalocyanine,
Tetrakis(2,6-diphenylphenoxy)dodecafluorovanadyl phthalo-cyanine,
Tetrakis(2,4-diphenylphenoxy)dodecafluorotitanyl phthalo-cyanine, Tetrakis(2,4,6-triphenylphenoxy) dodecafluorovanadyl phthalocyanine, Tetrakis(4-(2-(2-methoxyethoxy)carbonyl-6-methylphenoxy))-dodecafluorovanadyl phthalocyanine, Tetrakis(2-isopropoxycarbonyl-6-phenylphenoxy) dodeca-fluorovanadyl phthalocyanine, Tetrakis(2-(3-pentoxy)carbonyl-6-phenylphenoxy) dodeca-fluorovanadyl phthalocyanine, Tetrakis(2-(3-pentoxy)carbonyl-4-phenylphenoxy) dodeca-fluoro copper phthalocyanine, Tetrakis(2-tert-butoxycarbonyl-6-phenylphenoxy) dodeca-fluorovanadyl phthalocyanine, Tetrakis(2,4-diisopropoxycarbonyl-6-phenylphenoxy) dodeca-fluoro -phenylphenoxy)dodeca-fluoro iron phthalocyanine, Tetrakis(2-(2-butoxy)carbonyl-6-phenylphenoxy)dodeca-fluorovanadyl phthalocyanine, Tetrakis(2-(2-pentoxy)carbonyl-6-phenylphenoxy) dodeca-fluorovanadyl phthalocyanine, Tetrakis(2-(3-methoxyprpopoxy)carbonyl-6-phenylphenoxy)-dodecafluorovanadyl phthalocyanine, Tetrakis(2,4-di(2-methoxyethoxy)carbonyl-6-phenylphenoxy)-dodecafluoro nickel phthalocyanine, Tetrakis(2-ethoxy-6-phenylphenoxy) dodecafluorovanadyl phthalocyanine, Tetrakis(2,4-diethoxy-6-phenylphenoxy)dodecafluoro palladium phthalocyanine, Tetrakis(2-benzyloxycarbonyl-6-phenylphenoxy)dodeca-fluorotitanyl phthalocyanine, Tetrakis(2-phenetyloxycarbonyl-6-phenylphenoxy) dodeca-fluoro zinc phthalocyanine, Tetrakis(2-(2-tetrahydrofurfuryloxy)carbonyl-6-phenyl-phenoxy)dodecafluorotitanyl phthalocyanine, Tetrakis(4-(2-tetrahydrofurfuryloxy)carbonyl-6-phenyl-phenoxy)dodecafluoro palladium phthalocyanine, Tetrakis(2,4-di(2-tetrahydrofurfuryloxy)carbonyl-6-phenylphenoxy)dodecafluoro cobalt phthalocyanine, Tetrakis(6-(bromophenyl)-2-isopropoxycarbonyl-phenoxy)-dodecafluorovanadyl phthalocyanine, Tetrakis(bromo-2-isopropoxycarbonyl-6-phenylphenoxy)-dodecafluorovanadyl phthalocyanine, Tetrakis(6-(4-bromomethylphenyl)-2-(2-tetrahydrofurfuryloxy)carbonylphenoxy)dodecafluorotitanyl phthalocyanine, Tetrakis(6-(4-bromomethoxyphenyl)-2-(2-isopropoxy-carbonylphenoxy)dodecafluorovanadyl phthalocyanine, Tetrakis(2-(1,3-dibromo-2-propoxycarbonyl)-6-phenyl-phenoxy)dodecafluorovanadyl phthalocyanine, Tetrakis(2,4-di(6-bromohexyloxycarbonyl)-6-phenyl-phenoxy)dodecafluoro copper phthalocyanine, Tetrakis(2-(2-bromoethyl)-6-phenylphenoxy) dodecafluoro-vanadyl phthalocyanine, Tetrakis(4-(2-bromoethoxy)-2-isopropoxycarbonyl-6-phenyl-phenoxy)dodecafluoro iron phthalocyanine, Tetrakis(2-(2-bromoethoxy)-6-phenylphenoxy) dodecafluoro-vanadyl phthalocyanine, Tetrakis(2-(2-bromoethoxy)carbonyl-6-phenylphenoxy)-dodecafluorovanadyl phthalocyanine, Tetrakis(2-(1-bromo-2-propoxycarbonyl-6-phenylphenoxy)-dodecafluorovanadyl phthalocyanine, Tetrakisanilinododecafluoro iron phthalocyanine, Octakisphenylthiooctafluorovanadyl phthalocyanine, Tetrakis(p-methylphenoxy)-dodecafluoro copper phthalocyanine Octakis(2,4-xylylthio)octafluoro nickel phthalocyanine, Tetrakis(2,3,5,6-tetrafluorophenoxy)dodecafluoro iron phthalocyanine, Tetrakis(2,6-dichloroanilino)titanyl phthalocyanine, Octaphenoxyoctafluorovanadyl phthalocyanine, and Tetrakis(4-(p-methylphenoxy))-dodecachlorovanadyl phthalocyanine.

EXAMPLES

Example 1

[Production of tetrakis(2-(2-propoxy)carbonyl-6-phenylphenoxy)dodecafluorovanadyl phthalocyanine]

In a four-neck flask, 100 ml in inner volume, 4.36 g (0.01 mol) of 3,5,6-trifluoro-4-(2-(2-propoxy)carbonyl-6-phenylphenoxy) phthalonitrile, 0.225 g (1.5 mmol) of vanadium trioxide, 0.029 g (0.15 mmol) of p-toluene sulfonic acid hydrate, and 15 ml of benzonitrile were placed and left reacting therein at 190° C. for four hours. After the reaction, the reaction solution was distilled to expel the solvent and the solids consequently formed were washed with 200 ml of methyl alcohol, to obtain 3.62 g of a green cake [tetrakis (2-(2-propoxy)carbonyl-6-phenyl-phenoxy) dodecafluorovanadyl phthalocyanine)].

The yield from the phthalonitrile was 80%.

The visible absorption spectrum, solubility, and elemental analyses of the product aimed at are shown in Table 1 below.

TABLE 1

| Visible absorption spectrum Largest absorption wavelength in 2-ethoxyethanol = 715.0 nm ($\epsilon = 1.52 \times 10^5$) Thin film = 732.2 nm | | | | |
|---|---|---|---|---|
| Solubility in 2-ethoxyethanol | 15 wt. % | | | |
| Elemental analyses | C (%) | H (%) | N (%) | F (%) |
| Calculated | 63.62 | 3.34 | 6.18 | 12.58 |
| Found | 63.53 | 3.38 | 6.25 | 12.87 |

Example 2

[Production of tetrakis(2-(1,3-dibromo-2-propoxy)-carbonyl-6-phenylphenoxy)dodecafluorovanadyl phthalocyanine]

In a four-neck flask, 100 ml in inner volume, 5.94 g (0.01 mol) of 3,5,6-trifluoro-4-(2-(1,3-dibromo-2-propoxy) carbonyl-6-phenylphenoxy) phthalonitrile, 0.210 g (1.4 mmol) of vanadium trioxide, 0.057 g (0.3 mmol) of p-toluene sulfonic acid hydrate, and 15 ml of benzonitrile were placed and left reacting therein at 190° C. for four hours. After the reaction, the reaction solution was distilled to expel the solvent and the solids consequently formed were washed with 200 ml of methyl alcohol, to obtain 4.59 g of a green cake [tetrakis(2-(1,3-dibromo-2-propoxy)carbonyl-6-phenyl-phenoxy)dodecafluorovanadyl phthalocyanine)].

The yield from the phthalonitrile was 75%.

The visible absorption spectrum, solubility, and elemental analyses of the product aimed at are shown in Table 2 below.

TABLE 2

Visible absorption spectrum
Largest absorption wavelength in 2-ethoxyethanol =
714.5 nm ($\epsilon = 1.75 \times 10^5$)
Thin film = 731.6 nm

| Solubility in 2-ethoxyethanol | 14 wt. % | | | | |
|---|---|---|---|---|---|
| Elemental analyses | C (%) | H (%) | N (%) | F (%) | Br (%) |
| Calculated | 47.32 | 2.15 | 4.60 | 9.36 | 25.93 |
| Found | 47.65 | 2.24 | 4.47 | 9.51 | 25.46 |

Example 3

[Production of tetrakis(2-(2-methoxyethoxy)carbonyl-6-phenylphenoxy)dodecafluorovanadyl phthalocyanine]

In a four-neck flask, 100 ml in inner volume, 4.52 g (0.01 mol) of 3,5,6-trifluoro-4-(2-(2-methoxy-ethoxy)-carbonyl-6-phenyl-phenoxy) phthalonitrile, 0.225 g (1.5 mmol) of vanadium trioxide, 0.041 g (0.3 mmol) of salicylic acid, and 15 ml of benzonitrile were placed and left reacting therein at 190° C. for four hours. After the reaction, the reaction solution was distilled to expel the solvent and the solids consequently formed were washed with 200 ml of methyl alcohol, to obtain 1.97 g of a green cake [tetrakis(2-(2-methoxyethoxy)carbonyl-6-phenyl-phenoxy)dodecafluorovanadyl phthalocyanine].

The yield from the phthalonitrile was 42%.

The visible absorption spectrum, solubility, and elemental analyses of the product aimed at are shown in Table 3 below.

TABLE 3

Visible absorption spectrum
Largest absorption wavelength in 2-ethoxyethanol = 713.7 nm ($\epsilon = 1.42 \times 10^5$)
Thin film = 730.6 nm

| Solubility in 2-ethoxyethanol | 15 wt. % | | | |
|---|---|---|---|---|
| Elemental analyses | C (%) | H (%) | N (%) | F (%) |
| Calculated | 61.45 | 3.22 | 5.97 | 12.15 |
| Found | 62.71 | 3.13 | 6.08 | 11.97 |

Example 4

[Production of tetrakis(2-(2-tetrahydrofurfuryloxy)-carbonyl-6-phenylphenoxy)dodecafluorovanadyl phthalocyanine]

In a four-neck flask, 100 ml in inner volume, 4.78 g (0.01 mol) of 3,5,6-trifluoro-4-(2-(2-tetrahydrofurfuryloxy) carbonyl-6-phenylphenoxy) phthalonitrile, 0.225 g (1.5 mmol) of vanadium trioxide, 0.019 g (0.15 mmol) of quinoline, and 15 ml of benzonitrile were placed and left reacting therein at 190° C. for six hours. After the reaction, the reaction solution was distilled to expel the solvent and the solids consequently formed were washed with 200 ml of methyl alcohol, to obtain 1.88 g of a green cake [tetrakis (2-(2-tetrahydrofurfuryloxy) -carbonyl-6-phenylphenoxy) dodecafluorovanadyl-phthalocyanine].

The yield from the phthalonitrile was 38%.

The visible absorption spectrum, solubility, and elemental analyses of the product aimed at are shown in Table 4 below.

TABLE 4

Visible absorption spectrum
Largest absorption wavelength in 2-ethoxyethanol = 714.7 nm ($\epsilon = 1.22 \times 10^5$)
Thin film = 732.3 nm

| Solubility in 2-ethoxyethanol | 15 wt. % | | | |
|---|---|---|---|---|
| Elemental analyses | C (%) | H (%) | N (%) | F (%) |
| Calculated | 63.07 | 3.46 | 5.66 | 11.51 |
| Found | 62.37 | 3.61 | 5.83 | 10.88 |

Example 5

[Production of tetrakis(2-(2-methoxyethoxy)carbonyl-6-methylphenoxy)dodecafluorovanadyl phthalocyanine]

In a four-neck flask, 100 ml in inner volume, 3.90 g (0.01 mol) of 3,5,6-trifluoro-4-(2-(2-methoxyethoxy)-carbonyl-6-methyl-phenoxy) phthalonitrile, 0.273 g (1.5 mmol) of vanadium pentoxide, 0.057 g (0.3 mmol) of p-toluenesulfonic acid-hydrate, and 15 ml of benzonitrile were placed and left reacting therein at 190° C. for six hours. After the reaction, the reaction solution was distilled to expel the solvent and the solids consequently formed were washed with 200 ml of methyl alcohol, to obtain 1.75 g of a green cake [tetrakis(2-(2-methoxyethoxy)-carbonyl-6-methylphenoxy)dodecafluoro-vanadyl phthalocyanine].

The yield from the phthalonitrile was 43%.

The visible absorption spectrum, solubility, and elemental analyses of the product aimed at are shown in Table 5 below.

TABLE 5

Visible absorption spectrum
Largest absorption wavelength in 2-ethoxyethanol = 710.4 nm ($\epsilon = 1.32 \times 10^5$)
Thin film = 732.8 nm

| Solubility in 2-ethoxyethanol | 15 wt. % | | | |
|---|---|---|---|---|
| Elemental analyses | C (%) | H (%) | N (%) | F (%) |
| Calculated | 56.06 | 3.22 | 6.88 | 14.00 |
| Found | 57.38 | 3.31 | 6.46 | 13.67 |

Example 6

[Production of tetrakis(2-(2-ethoxyethoxy)carbonyl-6-methoxyphenoxy)dodecafluorovanadyl phthalocyanine]

In a four-neck flask, 100 ml in inner volume, 4.04 g (0.01 mol) of 3,5,6-trifluoro-4-(2-(2-ethoxyethoxy)-carbonyl-6-methoxy-phenoxy) phthalonitrile, 0.225 g (1.5 mmol) of vanadium trioxide, 0.029 g (0.30 mmol) of sulfuric acid, and 15 ml of benzonitrile were placed and left reacting therein at 190° C. for ten hours. After the reaction, the reaction solution was distilled to expel the solvent and the solids consequently formed were washed with 200 ml of methyl alcohol, to obtain 1.47 g of a green cake [tetrakis(2-(2-ethoxyethoxy)carbonyl-6-methoxy-phenoxy)dodecafluoro-vanadyl phthalocyanine].

The yield from the phthalonitrile was 35%.

The visible absorption spectrum, solubility, and elemental analyses of the product aimed at are shown in Table 6 below.

TABLE 6

Visible absorption spectrum
Largest absorption wavelength in 2-
ethoxyethanol = 715.2 nm ($\epsilon = 1.37 \times 10^5$)
Thin film = 733.0 nm

| Solubility in 2-ethoxyethanol | 13 wt. % | | | |
|---|---|---|---|---|
| Elemental analyses | C (%) | H (%) | N (%) | F (%) |
| Calculated | 57.05 | 3.59 | 6.65 | 13.54 |
| Found | 57.11 | 3.62 | 6.63 | 13.48 |

Example 7
[Production of hexadecafluorovanadyl phthalocyanine]

In a four-neck flask, 100 ml in inner volume, 2.00 g (0.01 mol) of tetrafluoro phthalonitrile, 0.225 g (1.5 mmol) of vanadium trioxide, 0.086 g (0.45 mmol) of p-toluene sulfonic acid-hydrate, and 15 ml of benzonitrile were placed and left reacting therein at 190° C. for 20 hours. After the reaction, the reaction solution was distilled to expel the solvent and the solids consequently formed were washed with 200 ml of methyl alcohol, to obtain 1.52 g of a green cake [hexadecafluorovanadyl phthalocyanine].

The yield from the phthalonitrile was 70%.

The visible absorption spectrum and elemental analyses of the product aimed at are shown in Table 7 below.

TABLE 7

Visible absorption spectrum
Largest absorption wavelength in 1-
chloronaphthalene = 710.2 nm ($\epsilon = 1.89 \times 10^5$)

| Elemental analyses | C (%) | N (%) | F (%) |
|---|---|---|---|
| Calculated | 44.32 | 12.92 | 35.05 |
| Found | 43.99 | 13.13 | 33.15 |

Example 8
[Production of hexadecafluorovanadyl phthalocyanine]

In a four-neck flask, 100 ml in inner volume, 2.00 g (0.01 mol) of tetrafluoro phthalonitrile, 0.236 g (1.3 mmol) of vanadium pentoxide, 0.086 g (0.45 mmol) of p-toluene sulfonic acid-hydrate, and 15 ml of benzonitrile were placed and left reacting therein at 190° C. for ten hours. After the reaction, the reaction solution was distilled to expel the solvent and the solids consequently formed were washed with 200 ml of methyl alcohol, to obtain 1.00 g of a green cake [hexadecafluorovanadyl phthalocyanine].

The yield from the phthalonitrile was 46%.

The visible absorption spectrum and elemental analyses of the product aimed at are shown in Table 8 below.

TABLE 8

Visible absorption spectrum
Largest absorption wavelength in 1-
chloronaphthalene = 710.1 nm ($\epsilon = 1.77 \times 10^5$)

| Elemental analyses | C (%) | N (%) | F (%) |
|---|---|---|---|
| Calculated | 44.32 | 12.92 | 35.05 |
| Found | 44.05 | 12.93 | 33.75 |

Example 9
[Production of tetrakis(2-(2-methoxyethoxy)carbonyl-6-methylphenoxy)dodecachlorovanadyl phthalocyanine]

In a four-neck flask, 100 ml in inner volume, 4.40 g (0.01 mol) of 3,5,6-trichloro-4-(2-(2-methoxy-ethoxy)carbonyl-6-methylphenoxy) phthalonitrile, 0.225 g (1.5 mmol) of vanadium trioxide, 0.095 g (0.5 mmol) of p-toluene sulfonic acid-hydrate, and 15 ml of benzonitrile were placed and left reacting therein at 190° C. for six hours. After the reaction, the reaction solution was distilled to expel the solvent and the solids consequently formed were washed with 200 ml of methyl alcohol, to obtain 3.16 g of a green cake [tetrakis(2-(2-methoxyethoxy)-carbonyl-6-methylphenoxy)-dodecachlorovanadyl phthalocyanine].

The yield from the phthalonitrile was 72%.

The visible absorption spectrum and elemental analyses of the product aimed at are shown in Table 9 below.

TABLE 9

Visible absorption spectrum
Largest absorption wavelength in 2-
ethoxyethanol = 712.5 nm ($\epsilon = 1.10 \times 10^5$)
Thin film = 732.0 nm

| Elemental analyses | C (%) | H (%) | N (%) | F (%) |
|---|---|---|---|---|
| Calculated | 51.90 | 2.98 | 6.37 | 24.17 |
| Found | 51.94 | 2.93 | 6.30 | 24.06 |

Example 10
[Synthesis of octakisphenylthiooctafluorovanadyl phthalocyanine (abbreviation: VOPc (PhS)$_8$F$_8$)]

In a four-neck flask, 100 ml in inner volume, 10 g (26.2 mmol) of 3,6-difluoro-4,5-bisphenylthio phthalonitrile, 0.6 g (4 mmol) of vanadium trioxide, 0.19 g (1 mmol) of p-toluene sulfonic acid-hydrate, and 50 ml of benzonitrile were placed and left reacting at 190° C. for five hours. Then, the reaction solution was cooled. A green solid substance consequently formed was filtered and washed with acetone, to obtain 31.5 g of VOPc(PhS)$_8$F$_8$.

The yield from the 3,6-difluoro-4,5-bisphenylthio phthalonitrile was 76 mol. %.

The visible absorption spectrum and elemental analyses of the product aimed at are shown in Table 10 below.

TABLE 10

Visible absorption spectrum
Largest absorption wavelength in toluene = 770 nm

| Elemental analyses | C (%) | H (%) | N (%) | S (%) | F (%) |
|---|---|---|---|---|---|
| Calculated | 60.48 | 2.54 | 7.05 | 16.15 | 9.75 |
| Found | 60.45 | 2.49 | 7.08 | 16.09 | 9.78 |

Example 11
[Synthesis of octaphenoxyoctafluorovanadyl phthalocyanine (abbreviation: VOPc(PhO) $_8$F$_8$)]

In a four-neck flask, 100 ml in inner volume, 9.12 g (26.2 mmol) of 3,6-difluoro-4,5-bisphenoxy phthalonitrile, 0.6 g (4 mmol) of vanadium trioxide, 0.19 g (1 mmol) of p-toluene sulfonic acid-hydrate, and 50 ml of benzonitrile were placed and left reacting at 190° C. for five hours. Then, the reaction solution was cooled. A green solid substance consequently formed was filtered and washed with acetone, to obtain 27.8 g of VOPc(PhO)$_8$F$_8$.

The yield from the 3,6-difluoro-4,5-bisphenoxy phthalonitrile was 73%.

The visible absorption spectrum and elemental analyses of the product aimed at are shown in Table 11 below.

TABLE 11

Visible absorption spectrum
Largest absorption wavelength in acetone = 720 nm

| Elemental analyses | C (%) | H (%) | N (%) | F (%) |
|---|---|---|---|---|
| Calculated | 65.81 | 2.76 | 7.67 | 10.41 |
| Found | 65.76 | 2.72 | 7.71 | 10.46 |

Example 12

[Production of hexadecachlorovanadylphthalocyanine]

In a four-neck flask, 100 ml in inner volume, 2.66 g (0.01 mol) of tetrachloro phthalonitrile, 0.194 g (1.3 mmol) of vanadium trioxide, 0.095 g (0.50 rnmol) of p-toluene sulfuric acid-hydrate, and 15 ml of benzonitrile were placed and left reacting therein at 190° C. for ten hours. After the reaction, the reaction solution was distilled to expel the solvent and the solids consequently formed were washed with 200 ml of methyl alcohol, to obtain 2.12 g of a green cake [hexadecachlorovanadylphthalocyanine].

The yield from the phthalonitrile was 75%.

The visible absorption spectrum and elemental analyses of the product aimed at are shown in Table 12 below.

TABLE 12

Visible absorption spectrum
Largest absorption wavelength in 1-chloronaphthalene = 712.4 nm ($\epsilon = 1.65 \times 10^5$)

| Elemental analyses | C (%) | N (%) | Cl (%) |
|---|---|---|---|
| Calculated | 34.00 | 9.91 | 50.17 |
| Found | 34.12 | 9.88 | 50.09 |

Example 13

[Production of titanylphthalocyanine]

In a four-neck flask, 100 ml in inner volume, 1.28 g (0.01 mol) of orthophthalonitrile, 0.240 g (3.0 mmol) of titanium dioxide, 0.095 g (0.50 mmol) of p-toluene sulfonic acid-hydrate, and 15 ml of benzonitrile were placed and left reacting therein at 190° C. for ten hours. After the reaction, the reaction solution was distilled to expel the solvent and the solids consequently formed were washed with 200 ml of methyl alcohol, to obtain 0.86 g of a green cake [titanylphthalocyanine].

The yield from the phthalonitrile was 60%.

The visible absorption spectrum and elemental analyses of the product aimed at are shown in Table 13 below.

TABLE 13

Visible absorption spectrum
Largest absorption wavelength in 1-chloronaphthalene = 710.5 nm ($\epsilon = 1.33 \times 10^5$)

| Elemental analyses | C (%) | H (%) | N (%) |
|---|---|---|---|
| Calculated | 66.68 | 2.80 | 19.44 |
| Found | 66.59 | 2.84 | 19.38 |

Example 14

[Production of tetrakis(2-(2-ethoxyethoxy) dodecafluorovanadyl phthalocyanine]

In a four-neck flask, 100 ml in inner volume, 0.225 g (1.5 mol) of vanadium trioxide, 0.076 g (0.40mmol) of p-toluene sulfonic acid-hydrate, and 15 ml of benzonitrile were placed and left reacting therein at 190° C. for one hour. Then, 2.70 g (0.01 mol) of 3,5,6-tri fluoro-4-(2-ethoxyethoxy)-phthalonitrile was added to the reaction mixture and left reacting at 190° C. for eight hours. After the reaction, the reaction solution was distilled to expel the solvent and the solids consequently formed were washed with 200 ml of methyl alcohol, to obtain 2.05 g of a green cake [tetrakis (2-(2-ethoxyethoxy) dodecafluorovanadyl phthalocyanine].

The yield from the phthalonitrile was 75%.

The visible absorption spectrum and elemental analyses of the product aimed at are shown in Table 14 below.

TABLE 14

Visible absorption spectrum
Largest absorption wavelength in 2-ethoxyethanol = 709.0 nm ($\epsilon = 1.26 \times 10^5$)

| Elemental analyses | C (%) | H (%) | N (%) | F (%) |
|---|---|---|---|---|
| Calculated | 52.56 | 3.31 | 10.22 | 20.79 |
| Found | 52.67 | 3.25 | 10.23 | 20.74 |

Control 1

In a four-neck flask, 100 ml in inner volume, 4.36 g (0.01 mol) of 3,5,6-trifluoro-4-(2-(2-propoxy)carbonyl-6-phenylphenoxy)phthalonitrile, 0.273 g (1.5 mmol) of vanadium pentoxide, and 15 ml of α-chloronaphthalene were placed and left reacting at 200° C. for four hours. The phthalocyanine compound aimed at was not obtained at all.

Control 2

In a four-neck flask, 100 ml in inner volume, 5.94 g (0.01 mol) of 3,5,6-trifluoro-4-(2-(1,3-dibromo-2-propoxy) carbonyl-6-phenylphenoxy) phthalocyanine, 0.273 g (1.5 mmol) of vanadium pentoxide, and 15 ml of ethylene glycol were placed and left reacting at 190° C. for four hours. The phthalocyanine compound aimed at was not obtained at all.

Control 3

Vanadium trioxide was used instead of vanadium pentoxide of control 1 and reacted with as control 1. The phthalocyanine compound aimed at was not obtained at all.

Control 4

Vanadium trichloride was used instead of vanadium pentoxide of control 1 and reacted with as control 1. The phthalocyanine compound aimed at was obtained with low yield of 8 wt %. The phthalocyanine compound obtained was included 2 wt % of chloride atoms.

The entire disclosure of Japanese Patent Application No. 9-148101 filed on Jun. 5, 1997, and Japanese Patent Application No.10-007020 filed on Jan. 16, 1998 including specification, claims, drawing and summary are incorporated herein by reference in its entirety.

What is claimed is:

1. A method for producing a phthalocyanine compound, which is characterized by causing an orthophthalo-nitrile compound possessable of substituent to react with metal oxide in the presence of an organic sulfonic acid compound in an organic solvent.

2. The method according to claim 1, wherein said orthophthalonitrile compound possessable of a substituent is the orthophthalonitrile compound having a substituent exhibiting smaller $\sigma_p$ values than $\sigma_m$ values in the Hammett's rule.

3. The method according to claim 2, wherein said substituent exhibiting smaller $\sigma_p$ values than $\sigma_m$ values in the Hammett's rule is at least one member selected from the class consisting of halogen atoms, —$R^1$, —$NHR^2$, —$NR^3R^4$, —$OR^5$, and —$SR^6$, and said each $R^1$—$R^6$ is an alkyl group or aryl group possessable of a substituent.

4. A method according to any of claim 1–3, wherein said metal oxide is the oxide of a metal having valency of not less than 2.

5. The method according to claim 4, wherein said metal oxide is a vanadium oxide.

6. The method according to claim 5, wherein said vanadium oxide is a vanadium trioxide.

7. The method according to claim 1, wherein said organic sulfonic compound is p-toluenesulfonic acid.

8. The method according to claim 1, wherein said organic solvent is at least one organic solvent selected from the group consisting of a nitrogenous solvent, a hydrocarbon solvent and a halogenated hydrocarbon solvent.

9. The method according to claim 7, wherein said organic solvent is nitrogenous solvent.

10. The method according to claim 9, wherein said nitrogenous solvent is benzonitrile.

* * * * *